United States Patent [19]

Engelbach et al.

[11] 4,110,370

[45] Aug. 29, 1978

[54] METHOD OF SEPARATING HIGH-BOILING OR NON-VOLATILE MATERIALS

[75] Inventors: Heinz Engelbach, Limburgerhof; Richard Krabetz, Kirchheim; Gerd Duembgen, Dannstadt-Schauernheim; Carl-Heinz Willersinn, Ludwigshafen; Walter Frey, Ludwigshafen; Ulrich Lebert, Ludwigshafen; Fritz Thiessen, Ludwigshafen, all of Fed. Rep. of Germany

[73] Assignee: BASF Aktiengesellschaft, Ludwigshafen, Fed. Rep. of Germany

[21] Appl. No.: 620,252

[22] Filed: Oct. 7, 1975

[30] Foreign Application Priority Data

Oct. 19, 1974 [DE] Fed. Rep. of Germany ....... 2449780

[51] Int. Cl.$^2$ .......................... C07C 57/04; B01D 1/14
[52] U.S. Cl. .......................... 260/530 N; 260/526 N; 260/533 N; 55/46; 203/42; 203/49; 203/DIG. 21
[58] Field of Search .................. 55/46, 48, 51; 260/526 N, 530 N, 533 N; 203/42, DIG. 21, DIG. 3, 49

[56] References Cited

U.S. PATENT DOCUMENTS

| 3,433,840 | 3/1969 | Shima et al. ....................... 203/42 |
| 3,868,417 | 2/1975 | Duembgen et al. ............. 260/526 N |
| 3,926,744 | 12/1975 | Noll et al. ....................... 260/526 N |
| 3,932,500 | 1/1976 | Duembgen et al. ............. 260/526 N |

Primary Examiner—Wilbur L. Bascomb, Jr.
Attorney, Agent, or Firm—Keil, Thompson & Shurtleff

[57] ABSTRACT

In the oxidation of propylene and/or acrolein, high-boiling or non-volatile byproducts are separated from the solvents used for absorbing the acrylic acid by treating the said solvents laden with byproducts with the hot reaction gases in such amounts that the major portion of the solvents evaporates, the residual solvent containing a high percentage of said byproducts then being discarded or worked up.

5 Claims, 1 Drawing Figure

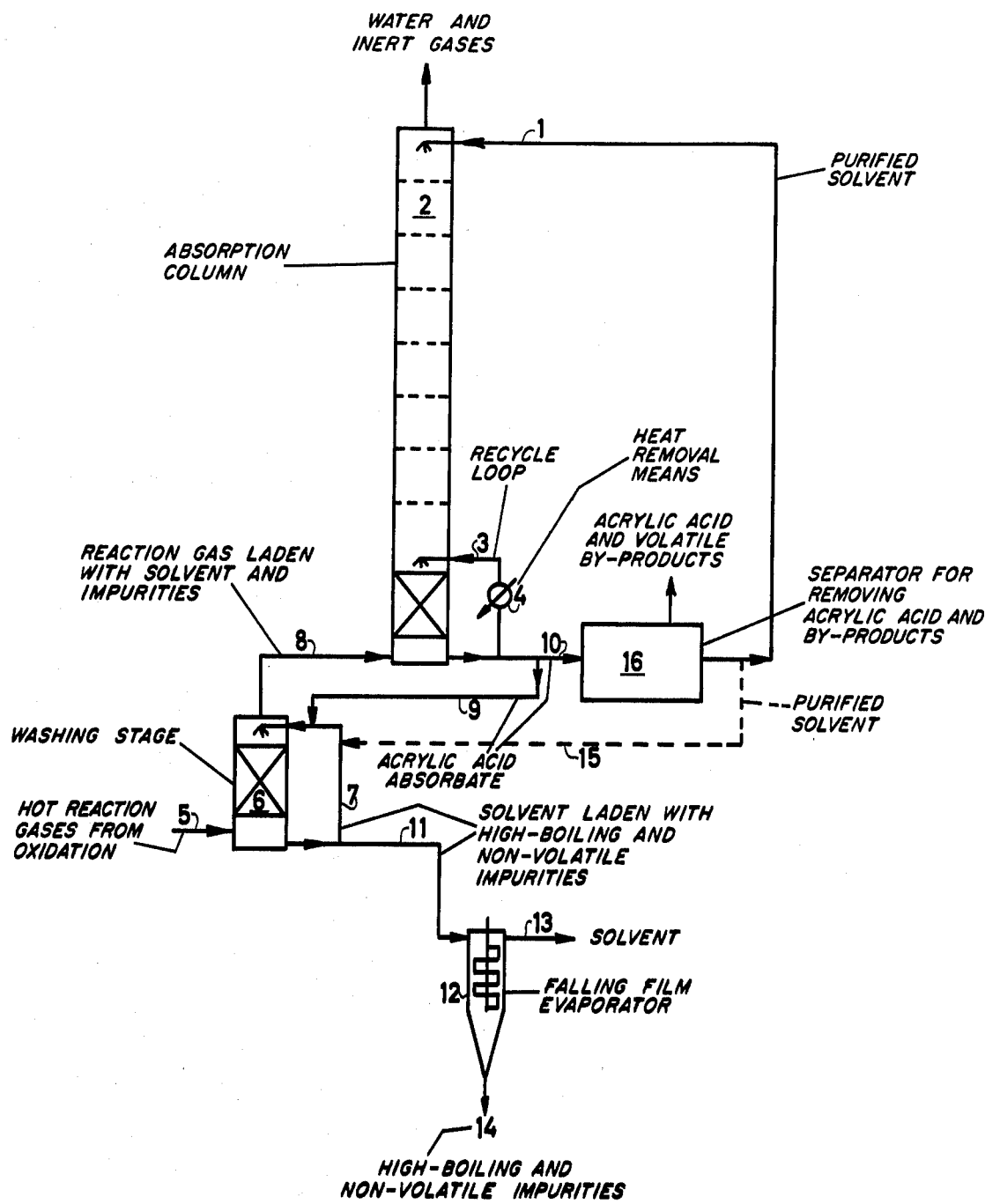

METHOD OF SEPARATING HIGH-BOILING OR NON-VOLATILE MATERIALS

The process of manufacturing acrylic acid by catalytic oxidation of propylene and/or acrolein with molecular oxygen is becoming increasingly significant. The acrylic acid is generally absorbed from the hot reaction gases with water or dilute aqueous acrylic acid solution. However, other processes are known in which acrylic acid is absorbed from the hot reaction gases coming from the oxidation of propylene and/or acrolein with the aid of high-boiling solvents. If, after separation of the acrylic acid absorbed in said high-boiling solvents, the said solvents are re-used for absorption of acrylic acid from the hot reaction gases, high-boiling or non-volatile products accumulate therein. With regard to this fact, German Published Application No. 2,136,396 mentions that the non-volatile or high-boiling products must be removed in order to avoid accumulation thereof in such circulating solvent. In this prior art process, a bleed stream of the solvent is purified by distillation in an evaporator prior to re-use for the absorption of acrylic acid. Examples of the high-boiling or non-volatile impurities are stabilizers which are added for the separation of the acrylic acid to prevent polymerization thereof. Furthermore, in spite of these stabilizers, polymeric acrylic acids usually form and are dissolved in the high-boiling solvents. Other impurities are cracked products of the solvent itself and of the stabilizers and also catalyst dust.

If the high-boiling solvents used for absorbing the acrylic acid from the hot reaction gases are not purified, incrustation and choking of the columns and other parts of the equipment are likely to occur so that only limited on-stream times are possible in practice.

Clearly, this type of trouble can be reduced if the portion of solvent which has been purified before recycling is increased. However, the need to purify the high-boiling solvent as far as possible is offset by the energy costs involved in purifying by distillation in conventional plants. There is thus a need to provide a high degree of purification of the circulated high-boiling solvents used for the absorption of the acrylic acid, at a minimum of energy additionally applied for said purification.

We have now found that non-volatile or high-boiling byproducts of the oxidation of propylene and/or acrolein may be particularly advantageously separated from the solvents used for absorbing the acrylic acid from the reaction gases, by purification of said solvents by distillation, provided the solvents laden with the non-volatile or high-boiling byproducts are contacted, prior to absorption of the acrylic acid, with the hot reaction gases in such amounts that the major portion of the solvents evaporates, whereupon the residual solvents containing accumulated non-volatile or high-boiling materials are separated and discarded or worked up.

Separation of the non-volatile or high-boiling materials from the solvents laden therewith may be advantageously carried out in a packed column or a column provided with baffles suitable for gas-liquid exchange. The solvents to be purified are fed to the top of the column, whilst the hot reaction gases from the propylene or acrolein oxidation flow upwardly countercurrently to the solvents over the said baffles or packing elements. It is not generally necessary to remove or apply heat. The solvent to be purified (a portion of the absorbate) is fed to such a washing stage from the outlet of the absorber at such a rate that the hot reaction gases become laden with solvent vapor, possibly to the point of saturation, whilst the non-volatile or high-boiling byproducts are discharged in the form of a concentrated solution in the solvent. Thus the evaporated portion of the solvent is purified without any additional energy costs and only the residual amount withdrawn with the accumulated byproducts needs to be worked up, e.g. by distillation, if recovery of the solvent or separation of the byproducts is of economical interest.

The steady temperature which results in such a washing stage may be designated as the cooling limit temperature. It is influenced, for example, by the temperature of the reaction gases on entering the washing stage, the specific heat of the reaction gas, the temperature of the acrylic acid absorbate fed to the stage, the type and amount of impurities in the absorbate and their vapor pressures, the heat of evaporation of the solvent, and the total pressure in the washing stage.

In the absorption of acrylic acid from the hot reaction gases coming from the oxidation of propylene or acrolein, it is usual to employ solvents which boil at much higher temperatures than acrylic acid, e.g. in the range of 200° to 360° C. Using such solvents, the cooling limit temperature resulting in a washing stage of the above kind under the above conditions is from 120° to 220° C. when operating at atmospheric pressure. Despite these relatively high temperatures, polymerization of the acrylic acid is not usually observed in such a washing stage.

In our novel purifying process for the solvents used in absorption the reaction gases coming from the oxidation of propylene or acrolein may be laden with the solvents to varying degrees. The amount of solvent required to reach saturation of the reaction gases depends on the amount of reaction gas present, the cooling limit temperature, the vapor pressure of the solvent at the cooling limit temperature and the total pressure in the washing stage. The vaporized portion of the solvent fed to the washing stage may be very high and is between 90 and 99.9%.

The content of non-volatile or high-boiling impurities in the washing stage is determined by the ratio of the amount of solvent required to saturate the reaction gas to the amount of solvent removed from the washing stage in liquid form (to be discarded or worked up) and to the proportion of high-boiling compounds produced in the process. Depending on the solubility of these high-boiling impurities in the solvent, accumulations thereof of up to 10% by weight or more may be achieved in the washing stage. This makes the withdrawal of the high-boiling or non-volatile impurities via the washing stage highly economical, since only a relatively small portion needs to be withdrawn from the washing stage in liquid form.

The accompanying drawing is an example of a flow sheet for the novel process. A solvent which boils at least 30° C. higher than acrylic acid is fed through line 1 to the acrylic acid absorption column 2 having at least one recycle loop 3 with heat removal means 4 and a bottom portion. The acrylic acid contained in the hot reaction gases coming from the oxidation of propylene or acrolein are washed from said gases by said solvent flowing countercurrently at a temperature above the dew point of water, as described for example in German Published Application 2,136,396. The major part of the water contained in the hot reaction gases and also the inert gases such as carbon monoxide, carbon dioxide and nitrogen, are not absorbed by the solvent and these can thus leave the column 2 as overheads. The hot reaction gas coming from the oxidation of propylene or acrolein is fed through line 5 to the washing stage 6 of the invention. In this washing stage, the solvent laden with high-boiling or non-volatile impurities may be circulated through loop 7 without external application or removal of heat. In the washing stage 6 the reaction gas becomes laden with the circulated solvent and any low-boiling materials additionally contained therein, according to the equilibrium partial pressure. Due to vaporization of the solvents (and any low-boilers), the reaction gas laden with such solvents (and high-boilers) cools to the cooling limit temperature. The gas, having cooled to said cooling limit temperature and laden with said impurities, leaves the washing stage 6 via line 8 and is fed to the bottom of the evaporation column 2. The absorption of the solvents (and any low-boilers) in the washing stage 6 by the hot reaction gases causes solvent (and any low-boilers) to be removed from the washing stage 6. At a rate corresponding to said rate of removal, fresh solvent to be purified (containing acrylic acid, high-boiling and non-volatile impurities and other by-products of the propylene or acrolein oxidation) is fed to the washing stage 6 via line 9 from the acrylic acid absorbate leaving the absorption column 2 via line 10, by which means the level of the bottoms of the wash column is kept constant. Low-boilers such as acrylic acid and acetic acid contained in the absorbate passing through line 9 evaporate immediately at the high temperature in the washing stage. High-boiling and non-volatile impurities passing to the washing stage accumulate in the solution circulated through loop 7. The high-boiling and non-volatile impurities are tapped from said loop together with some of the solvent through line 11. The material tapped off through line 11 may be destroyed, e.g. by combustion, or worked up by distillation. In the drawing, the material leaving the washing stage 6 through line 11 is fed to a falling film evaporator 12, from which the distilled solvent leaves through line 13 and the high-boiling and non-volatile impurities through line 14. The solvent losses are very low in this case. Instead of passing impure solvent through line 9 to the washing stage 6, it is possible to pass purified solvent through line 15 to said washing stage, said purified solvent being tapped from line 1 and consisting of solvent from which acrylic acid, acetic acid and any other byproducts have been removed in one or more separating stages 16. However, it is preferred to pass acrylic acid absorbate through line 9 to said washing stage 6. In a further embodiment of the process illustrated in the accompanying drawing, the washing stage 6 may be directly attached to the column 2, in a sense forming a part thereof.

Examples of solvents which are suitable for the absorption of acrylic acid from the hot reaction gases and which can be purified by our novel process are esters of benzoic acid and phthalic acid with straight-chain $C_{1-8}$ alkanols such as n-butyl benzoate, methyl benzoate, ethyl benzoate, dimethyl phthalate and diethyl phthalate, which melt below 30° C. and boil, at atmospheric pressure, at temperatures above 180°–400° C. and preferably at from 220° to 360° C., and so-called heat carriers such as diphenyl, diphenyl ethers and mixtures of diphenyl, diphenyl ethers or their chloro derivatives and triaryl alkanes, e.g. 4-methyl-4'-benzyl-diphenylmethane and its isomers 2-methyl-2'-benzyl-diphenylmethane, 2-methyl-4'-benzyl-diphenylmethane and 4-methyl-2'-benzyl-diphenylmethane and mixtures of said isomers. In the following examples, the apparatus used is one corresponding to that illustrated in the accompanying drawing and in which the acrylic acid is absorbed from the reacting gases in a conventional absorption column.

EXAMPLE 1

A mixture of 73.5% w/w of diphenyl ether and 26.5% w/w of diphenyl is fed at a rate of 450 kg/hr to the absorption column 2 via line 1. In the absorption column 2, the reaction gas coming from the catalytic propylene oxidation and containing 3% v/v of acrylic acid is passed countercurrently at a rate of 520 m³/hr (STP) at a temperature of from 50° to 70° C., and the acrylic acid is absorbed by said solvent mixture. The water contained in the reaction gas and insert gases such as nitrogen, carbon monoxide and carbon dioxide, and also oxygen are discharged from the absorption column as overheads. Before entering the absorption column 2, the reaction gas is passed to the washing stage 6 at a temperature of 250° C. The washing stage 6 consists of a column in which there is disposed a packet of angle sheets (arranged in grid form for good liquid distribution) and which is provided with a liquid loop (line 7) containing a pump. The pressure in the washing stage 6 is 1.1 atmospheres and the cooling limit temperature is 146° C. The reaction gas becomes laden with solvent and substances such as acrylic acid and acetic acid contained as low-boilers in the acrylic acid absorbate passed to the washing stage 6 through line 9.

In the washing stage 6 the reaction gas (520 m³/hr (STP)) becomes laden with 135 kg/hr of solvent in accordance with the vapor pressures of the solvent. A solution containing 6% w/w of materials boiling at above 400° C. at atmospheric pressure (high-boiling and non-volatile substances) is tapped from the washing stage 6 through line 11 at a rate of 0.5 kg/hr.

From the ratio of vaporized solvent to tapped solvent there can be calculated an accumulation factor for the high-boilers of 270, i.e. for the same steady content of high-boilers in the solvent loop it would be necessary to work up 270 times the amount of solvent if the washing stage 6 were not used.

EXAMPLE 2

Example 1 is repeated except that the reaction gas is fed to the washing stage at a temperature of 300° C. Under these conditions, the resulting cooling limit temperature in the washing stage 6 is 155° C. At this temperature, the reaction gas becomes loaded with 190 kg/hr of the solvent in the washing stage 6. Solution is again tapped from the washing stage 6 via line 11 at a rate of 0.5 kg/hr and the concentration of high-boilers in the washing stage again has a steady value of about 6% by weight.

EXAMPLE 3

Example 1 is repeated except that the solvent used is dimethyl phthalate. Under these conditions the cooling limit temperature resulting in the washing stage 6 is 165° C. At this temperature the reaction gas becomes loaded with 150 kg/hr in the washing stage 6. Solution is again tapped at a rate of 0.5 kg/hr from the washing stage 6 via line 11. The concentration of high-boilers in the washing stage is again about 6% by weight.

EXAMPLE 4

Example 1 is repeated except that the solvent used is a heat-carrying oil based on an isomeric mixture of triaryl alkanes such as 4-methyl-4'-benzyl-diphenylmethane having a boiling range of 380°–390° C. Due to the use of smaller apparatus, only 3 m$^3$/hr of reaction gas (STP) are fed to the absorption column and only 2.6 kg/hr of solvent are fed thereto via line 1. Under these conditions the resulting cooling limit temperature in the washing stage 6 is 210° C. At this temperature the reaction gas becomes loaded with 40 g/hr of solvent in the washing stage 6. Only 3 g/hr of solvent are removed from the washing stage 6 via line 11. The concentration of high-boilers in the washing stage 6 is about 6% by weight.

We claim:

1. In a process for separating acrylic acid from the hot reaction gas obtained from the manufacture of acrylic acid by catalytic oxidation of propylene and/or acrolein with molecular oxygen, said hot reaction gas containing acrylic acid and low-boiling impurities, wherein the acrylic acid and low-boiling impurities are absorbed with a solvent in a means for absorbing gases into solvents and high-boiling and non-volatile impurities are formed in said means, the solvent boiling in the range from about 200° to 360° C., and the solvent is re-used for absorption after being separated from the acrylic acid and low-boiling impurities, the improvment comprising:

(a) taking a portion of the solvent containing acrylic acid and high-boiling and non-volatile impurities, (b) contacting said portion of solvent with the hot reaction gas containing acrylic acid and low-boiling impurities in a means for gas-liquid exchange at such a rate that between about 90 and 99.9% of the solvent evaporates thereby producing a gas containing vaporized solvent, acrylic acid and low-boiling impurities and a residual solvent, the residual solvent containing the high-boiling and non-volatile impurities, (c) conducting the gas containing vaporized solvent, acrylic acid and low-boiling impurities to said means for absorbing gases into solvents with a means for conducting gas, and (d) separating the residual solvent from said means for gas-liquid exchange.

2. A process as set forth in claim 1, wherein the means for gas-liquid exchange is a packed column or a column provided with baffles suitable for gas-liquid exchange.

3. A process as set forth in claim 1, wherein the separated residual solvent containing high-boiling and non-volatile materials is distilled.

4. A process as set forth in claim 1, wherein the hot reaction gas is first cooled to about 120° C. to 220° C. in the means for gas-liquid exchange and then loaded with vaporized solvent, acrylic acid and low-boiling impurities.

5. A process as set forth in claim 1, wherein the acrylic acid and low-boiling impurities are absorbed by re-used solvent flowing countercurrently.

* * * * *